(12) United States Patent
DiFoggio et al.

(10) Patent No.: US 9,109,433 B2
(45) Date of Patent: Aug. 18, 2015

(54) EARLY KICK DETECTION IN AN OIL AND GAS WELL

(75) Inventors: Rocco DiFoggio, Houston, TX (US); Daniel Duncan Blue, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 557 days.

(21) Appl. No.: 13/401,503

(22) Filed: Feb. 21, 2012

(65) Prior Publication Data

US 2012/0170406 A1 Jul. 5, 2012

Related U.S. Application Data

(63) Continuation-in-part of application No. 12/398,060, filed on Mar. 4, 2009, now Pat. No. 8,794,062, which is a continuation-in-part of application No. 11/194,365, filed on Aug. 1, 2005, now Pat. No. 7,523,640, and a continuation-in-part of application No. 11/841,527, filed on Aug. 20, 2007, now abandoned.

(60) Provisional application No. 60/839,602, filed on Aug. 23, 2006.

(51) Int. Cl.
| | | |
|---|---|---|
| E21B 47/10 | (2012.01) |
| G01N 29/024 | (2006.01) |
| G01N 29/028 | (2006.01) |
| G01N 29/44 | (2006.01) |
| G01V 1/50 | (2006.01) |
| G01F 23/24 | (2006.01) |
| G01F 23/296 | (2006.01) |

(52) U.S. Cl.
CPC ............ *E21B 47/101* (2013.01); *E21B 47/1005* (2013.01); *G01F 23/247* (2013.01); *G01F 23/2961* (2013.01); *G01N 29/024* (2013.01); *G01N 29/028* (2013.01); *G01N 29/4418* (2013.01); *G01V 1/50* (2013.01); *G01N 2291/02818* (2013.01); *G01N 2291/02836* (2013.01); *G01N 2291/045* (2013.01)

(58) Field of Classification Search
USPC .......................................... 73/152.04, 152.18
See application file for complete search history.

(56) References Cited

U.S. PATENT DOCUMENTS

| | | |
|---|---|---|
| 2,244,484 A | 6/1941 | Beers |
| 3,776,032 A | 12/1973 | Vogel |

(Continued)

FOREIGN PATENT DOCUMENTS

| | | |
|---|---|---|
| WO | WO9850680 A2 | 11/1998 |

OTHER PUBLICATIONS

Bulloch, T. E.; The Investigation of Fluid Properties and Seismic Attributes for Reservoir Characterization, Thesis for degree of Master of Science in Geological Engineering, Michigan Technological University, 1999, pp. A1-A6.

(Continued)

*Primary Examiner* — John Fitzgerald
(74) *Attorney, Agent, or Firm* — Cantor Colburn LLP

(57) ABSTRACT

An apparatus, method and computer-readable medium for detecting a gas influx event in a borehole fluid during a drilling operation is disclosed. A measurement of an acoustic velocity of the borehole fluid is obtained at an acoustic sensor disposed in a borehole. A measurement of temperature of the borehole fluid is obtained at a temperature sensor disposed in the borehole. A process compares the measurement of the acoustic velocity of the borehole fluid to the measurement of the temperature of the borehole fluid to detect the gas influx event.

17 Claims, 17 Drawing Sheets

(56) References Cited

U.S. PATENT DOCUMENTS

| | | | |
|---|---|---|---|
| 4,208,906 A * | 6/1980 | Roberts, Jr. | 73/152.32 |
| 4,273,212 A | 6/1981 | Dorr et al. | |
| 4,412,130 A | 10/1983 | Winters | |
| 4,492,865 A | 1/1985 | Murphy et al. | |
| 4,571,693 A | 2/1986 | Birchak et al. | |
| 4,619,267 A | 10/1986 | Lannuzel et al. | |
| 4,733,232 A | 3/1988 | Grosso | |
| 4,769,793 A | 9/1988 | Kniest et al. | |
| 4,938,066 A | 7/1990 | Dorr | |
| 5,130,950 A | 7/1992 | Orban et al. | |
| 5,163,029 A | 11/1992 | Bryant et al. | |
| 5,275,040 A | 1/1994 | Codazzi | |
| 5,635,626 A | 6/1997 | Hammond et al. | |
| 5,741,962 A | 4/1998 | Birchak et al. | |
| 6,029,507 A | 2/2000 | Faber et al. | |
| 6,032,516 A | 3/2000 | Takahashi et al. | |
| 6,050,141 A | 4/2000 | Tello et al. | |
| 6,176,323 B1 | 1/2001 | Weirich et al. | |
| 6,205,848 B1 | 3/2001 | Faber et al. | |
| 6,208,586 B1 | 3/2001 | Rorden et al. | |
| 6,250,137 B1 | 6/2001 | Takahashi et al. | |
| 6,634,214 B1 | 10/2003 | Thurston et al. | |
| 6,648,083 B2 | 11/2003 | Evans et al. | |
| 6,672,163 B2 | 1/2004 | Han et al. | |
| 6,768,106 B2 | 7/2004 | Gzara et al. | |
| 6,817,229 B2 | 11/2004 | Han et al. | |
| 6,829,947 B2 | 12/2004 | Han et al. | |
| 6,957,572 B1 | 10/2005 | Wu | |
| 7,024,917 B2 | 4/2006 | DiFoggio | |
| 7,334,651 B2 | 2/2008 | Wu | |
| 2002/0100327 A1 | 8/2002 | Kersey et al. | |
| 2002/0117003 A1 | 8/2002 | Banno et al. | |
| 2002/0178787 A1 | 12/2002 | Matsiev et al. | |
| 2002/0178805 A1 | 12/2002 | DiFoggio et al. | |
| 2002/0184940 A1 | 12/2002 | Storm, Jr. et al. | |
| 2002/0189367 A1 | 12/2002 | Gomm et al. | |
| 2002/0194906 A1 | 12/2002 | Goodwin et al. | |
| 2003/0029241 A1 | 2/2003 | Mandal | |
| 2003/0029242 A1 | 2/2003 | Yaralioglu et al. | |
| 2003/0051533 A1 | 3/2003 | James et al. | |
| 2003/0101819 A1 | 6/2003 | Mutz et al. | |
| 2003/0144746 A1 | 7/2003 | Hsiung et al. | |
| 2003/0150262 A1 | 8/2003 | Han et al. | |
| 2003/0172734 A1 | 9/2003 | Greenwood | |
| 2003/0209066 A1 | 11/2003 | Goodwin | |
| 2003/0220742 A1 | 11/2003 | Niedermayr et al. | |
| 2004/0007058 A1 | 1/2004 | Rylander et al. | |
| 2004/0020294 A1 | 2/2004 | Buckin | |
| 2004/0040746 A1 | 3/2004 | Niedermayr et al. | |
| 2004/0060345 A1 | 4/2004 | Eggen et al. | |
| 2004/0095847 A1 | 5/2004 | Hassan et al. | |
| 2004/0173017 A1 | 9/2004 | O'Brien | |
| 2004/0194539 A1 | 10/2004 | Gysling | |
| 2004/0216515 A1 | 11/2004 | Yakhno et al. | |
| 2004/0236512 A1 | 11/2004 | DiFoggio et al. | |
| 2005/0103097 A1 | 5/2005 | Faltum et al. | |
| 2005/0149277 A1 | 7/2005 | Bailey et al. | |
| 2005/0212869 A1 | 9/2005 | Ellson et al. | |
| 2005/0223808 A1 | 10/2005 | Myers et al. | |
| 2005/0252294 A1 | 11/2005 | Ariav | |
| 2005/0268703 A1 | 12/2005 | Funck et al. | |
| 2007/0022803 A1 | 2/2007 | DiFoggio et al. | |
| 2008/0047337 A1 | 2/2008 | Chemali et al. | |
| 2009/0173150 A1 | 7/2009 | DiFoggio et al. | |
| 2009/0272580 A1 | 11/2009 | Dolman et al. | |
| 2010/0315900 A1 | 12/2010 | DiFoggio et al. | |

OTHER PUBLICATIONS

Doyle, E.F. et al.; "Plan for Surprises: Pore Pressure Challenges during the drilling of a Deepwater Exploration Well in mid-winter in Norway," SPE/IADC 79848, SPE/IADC Drilling Conference, Amsterdam, The Netherlands, Feb. 19-21, 2003, pp. 1-8.

Guyod, Hubert; "Temperature Well Logging," Oil Weekly, Well Logging, Part 6, 1946, pp. 40-44.

Havira, R. M.; "Ultrasonic Cement Bond Evaluation," Paper N, SPWLA Twenty-Third Annual Logging Symposium, Jul. 6-9, 1982, pp. 1-11.

Honarvar, F. et al.; Reference wavelets used for deconvolution of ultrasonic time-of-flight diffraction (ToFD) signals, 17th World Conference on Nondestructive Testing, Oct. 25-28, 2008, Shanghai, China, pp. 1-9.

Kading, Horace W. et al.; "Temperature Surveys: The Art of Interpretation," Am. Pet. Inst., Pub.; (United States); Journal vol. 906-14-N; Conference; API southwestern district product division spring meeting, Lubbock, Texas, USA, Mar. 12, 1969, pp. 1-20.

Mohanty, Sitakanta; "Effect of Multiphase Fluid Saturation on the Thermal Conductivity of Geologic Media," J. Phys. D. Appl. Phys., 30, No. 24 (Dec. 21, 1997), pp. L-80-L84.

Reservoir Characterization Instrument, RCI Instrument Modules, pamphlet from Baker Hughes, Copyright 2000 Baker Hughes Incorporated, pp. 7-1-7-11.

Reservoir Characterization Instrument, RCI Instrument Modules, pamphlet from Baker Hughes, Copyright 2000 Baker Hughes Incorporated, pp. 7-12-7-20.

Reservoir Characterization Instrument, RCI Instrument Modules, pamphlet from Baker Hughes, Copyright 2000 Baker Hughes Incorporated, pp. 7-21-7-28.

Savitzky, A. et al.; "Smoothing and Differentiation of Data by Simplified Least Squares Procedures," Analytical Chemistry, International Gas Chromatography Symposium, vol. 36, No. 8, Jul. 1964, pp. 1627-1639

Weatherford, "HEL MWD System-Rapid Annular Temperature (RAT) Sensor," http://www.weatherford.com/weatherford/groups/web/documents/weatherfordcorp/wft104872.pdf, 2 sheets.

International Search Report and Written Opinion dated Jun. 12, 2013 for International Application No. PCT/US2013/026832.

* cited by examiner

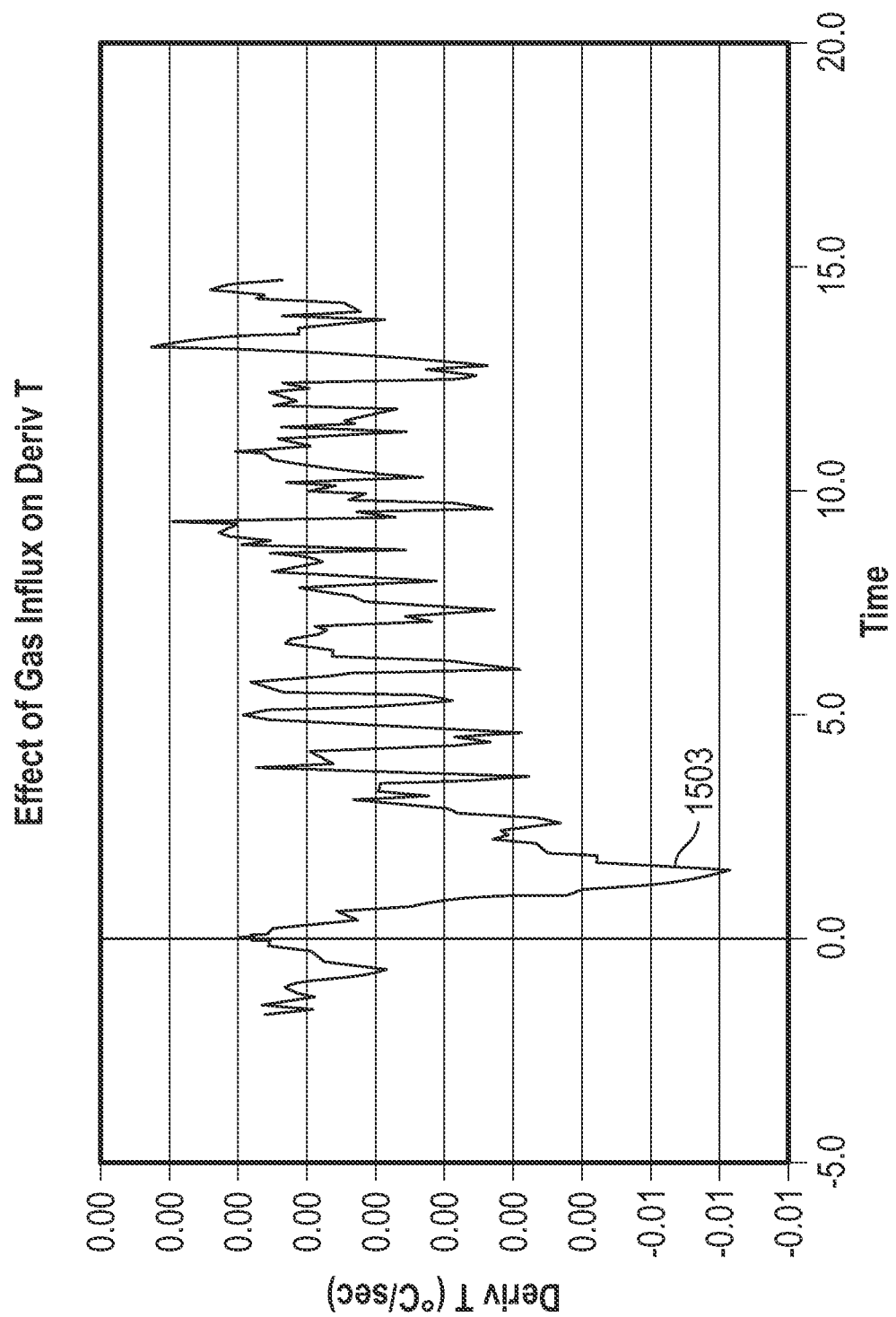

EARLY KICK DETECTION IN AN OIL AND GAS WELL

CROSS-REFERENCES TO RELATED APPLICATIONS

This application is a continuation-in-part of U.S. patent application Ser. No. 12/398,060, filed on Mar. 4, 2009, which is a continuation-in-part of U.S. patent application Ser. No. 11/841,527, filed Aug. 20, 2007, and U.S. patent application Ser. No. 11/194,365, now U.S. Pat. No. 7,523,640; and further claims priority from U.S. Provisional Patent Application Ser. No. 60/839,602 filed on Aug. 23, 2006.

BACKGROUND OF THE DISCLOSURE

1. Field of the Disclosure

This disclosure relates generally to oil and gas well logging tools. More particularly, this disclosure relates to tools and methods for identifying the influx of gas into the borehole in real-time during drilling operations.

2. Description of the Related Art

Exploration for hydrocarbons commonly includes using a bottomhole assembly including a drill-bit for drilling a borehole in an earth formation. Drilling fluid or "mud" used in the drilling may vary in density or "mud weight" for a number of reasons. Such variations can result from changes in the quantity and density of cuttings (particles of formation); changes in the "mud program" at the surface, changes in temperature, etc. Variations in mud density also occur when gas or liquid enter the borehole from the formation. Such influx of formation fluids may likely be the result of formation overpressures or abnormally high pressures.

Pressure detection concepts are especially important in drilling. Not only does the drilling rate decrease with a high overbalance of mud pressure versus formation pressure, but also lost circulation and differential pressure sticking of the drill pipe can readily occur. More importantly, an underbalance of mud pressure versus formation pressure can cause a pressure "kick." A well may kick without forewarning. Balanced drilling techniques often require only a fine margin between effective pressure control and a threatened blowout. Additionally, there are situations where underbalance is maintained to avoid formation damage so that it is important to detect inflow of formation liquids into the borehole.

Some prior art techniques for detecting abnormal formation pressure are based on measurement of drilling parameters such as drilling rate, torque and drag; drilling mud parameters such as mud gas cuttings, flow line mud weight, pressure kicks, flow line temperature, pit level and pit volume, mud flow rate; shale cutting parameters such as bulk density, shale factor, volume and size of cuttings. A drawback of some of these measurements is that they are not available in real-time but one must wait for the bottom hole fluid to reach the surface.

Other prior art methods for identifying possible kicks rely on density measurements of the borehole fluid. See, for example, U.S. Pat. No. 4,492,865 to Murphy et al., U.S. Pat. No. 4,412,130 to Winters, U.S. Pat. No. 6,648,083 to Evans et al., and U.S. Pat. No. 6,768,106 to Gzara et al. A drawback of methods that make density measurements is that gas must be present in sufficient quantities to affect the density of the mud, so that dissolved gas that may be a precursor to a gas kick would not register with conventional density measuring devices. In addition, the density measurements made by the prior art devices are responsive to varying degrees to the density of the formation. They also require the use of a radioactive source—a safety hazard during drilling operations.

There is a need for a technique to measure the properties of the borehole fluid downhole with a single tool in order to detect kicks and inflow of formation liquids. The present disclosure satisfies this need.

SUMMARY OF THE DISCLOSURE

In one aspect, the present disclosure provides a method of detecting a gas influx event in a borehole fluid during drilling operations that includes: obtaining a measurement of an acoustic velocity of the borehole fluid at an acoustic sensor disposed in a borehole; obtaining a measurement of temperature of the borehole fluid at a temperature sensor disposed in the borehole; and comparing the measurement of the acoustic velocity of the borehole fluid to the measurement of the temperature of the borehole fluid to detect the gas influx event.

In another aspect, the present disclosure provides an apparatus for detecting a gas influx event in a borehole fluid during drilling operation that includes: an acoustic sensor configured to obtain a measurement of an acoustic velocity of the borehole fluid; a temperature measuring device configured to obtain a measurement of a temperature of the borehole fluid; and a processor configured to compare the measurement of the acoustic velocity of the borehole fluid to the measurement of the temperature of the borehole fluid to determine a gas influx event.

In yet another aspect, the present disclosure provides a computer-readable medium having a set of instruction stored thereon that when read by a processor enable the processor to perform a method, the method including: receiving a measurement of an acoustic velocity of a borehole fluid from an acoustic sensor disposed in a borehole; receiving a measurement of temperature of the borehole fluid from a temperature sensor disposed in the borehole; and comparing the measurement of the acoustic velocity of the borehole fluid to the measurement of the temperature of the borehole fluid to detect a gas influx event.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

The present disclosure is best understood with reference to the accompanying figures in which like numerals refer to like elements and in which:

FIG. 15B shows a graph of a change in borehole fluid temperature values over time.

DETAILED DESCRIPTION OF THE DISCLOSURE

Figure 1:
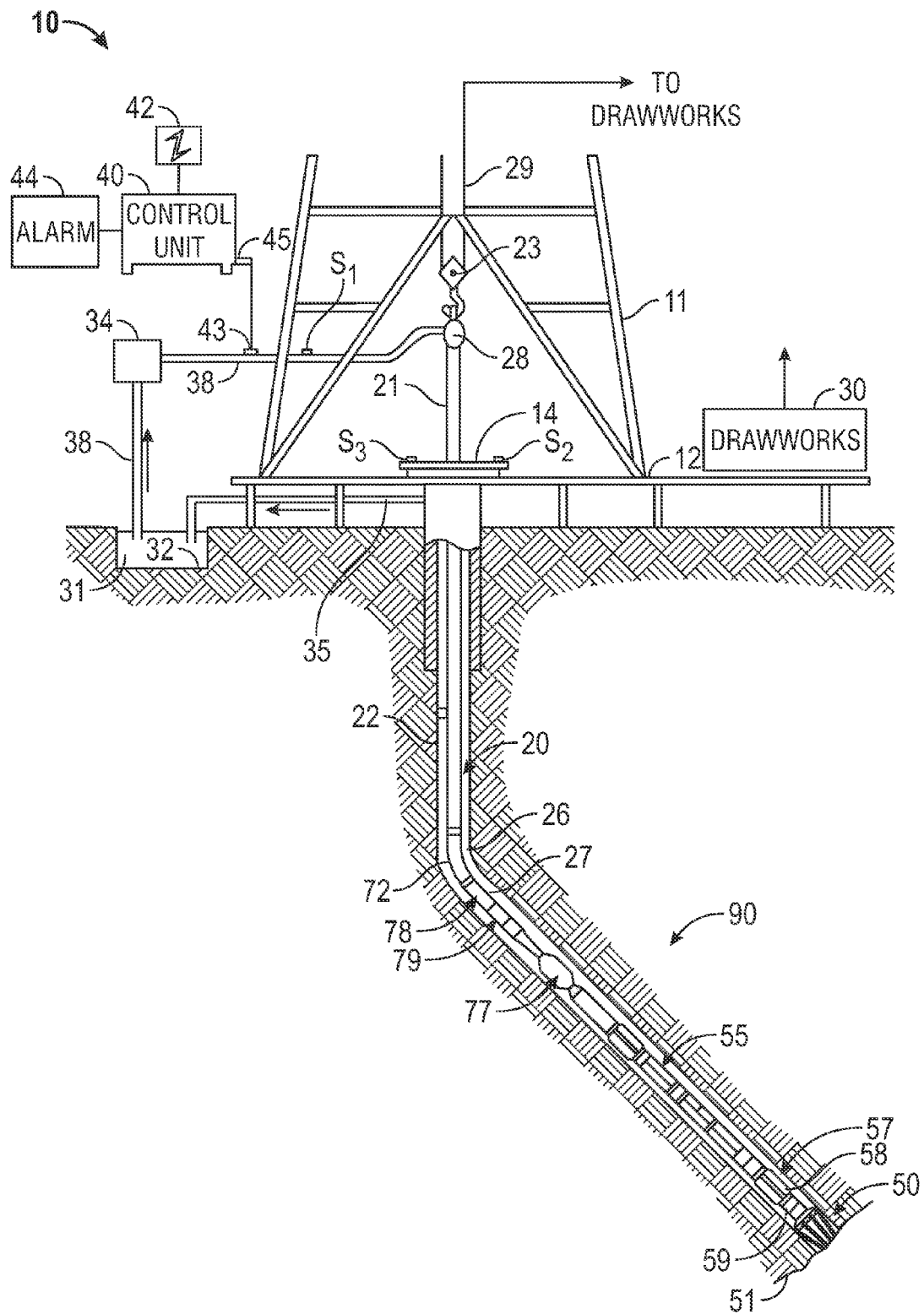
FIG. 1 (Prior Art) shows a measurement-while-drilling tool suitable for use with the present disclosure.

FIG. 1 shows a schematic diagram of a drilling system 10 with a drillstring 20 carrying a drilling assembly 90 (also referred to as the bottom-hole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein.

During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

Figure 2:
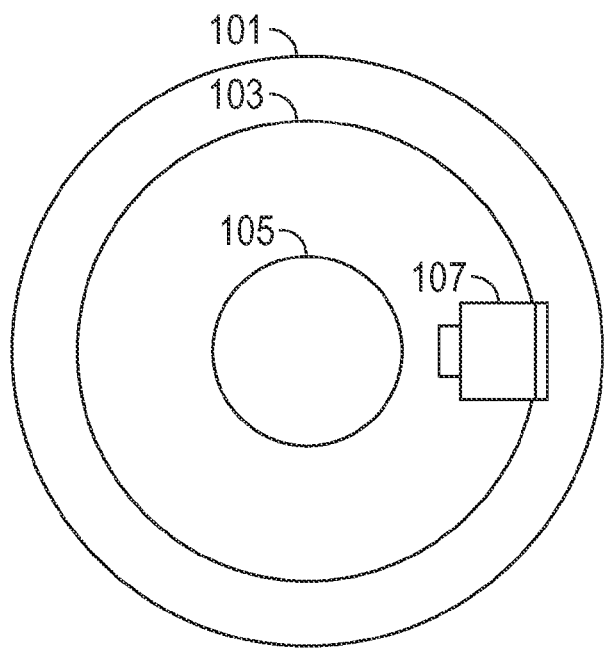
FIG. 2 is a cross sectional view of a measurement sub of the present disclosure.

Turning now to FIG. 2, a cross-section of an acoustic sub that can be used for determining the formation density is illustrated. The drill collar is denoted by 103 and the borehole wall by 101. An acoustic transducer assembly 107 is positioned inside the drill collar.

Figure 3:
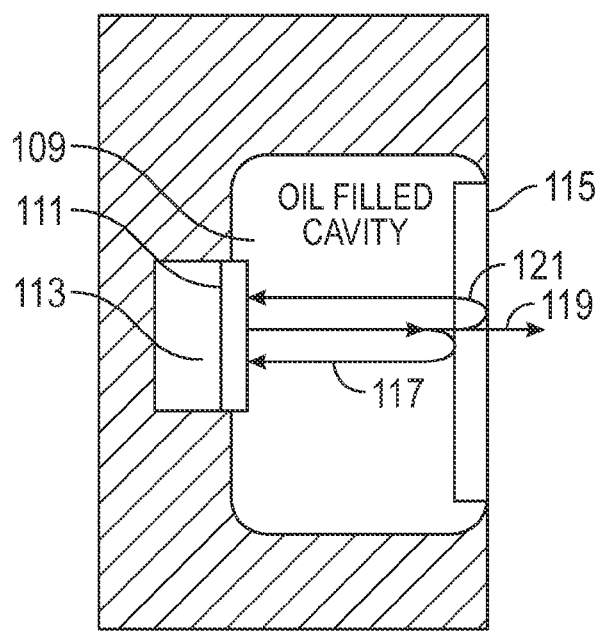
FIG. 3 is a detailed sectional view of the acoustic transducer in FIG. 2.

As shown in FIG. 3, the acoustic transducer assembly includes an fluid-filled cavity 109. An acoustic transducer 111 such as a piezoelectric transducer is positioned at one side of the cavity 109. On the other side of the cavity 109 is a sensor plate 115. The cavity is filled with a fluid with known density and compressional wave velocity. The plate 115 has a known thickness, compressional wave velocity and density.

As shown in FIG. 3, activation of the transducer generates acoustic waves in the fluid. Exemplary raypaths resulting from the excitation are shown in FIG. 3. The ray path 117, for example, corresponds to an acoustic wave that is reflected from the inner wall of the sensor plate. The raypath 121 corresponds to an acoustic wave that is reflected from the outer surface of the sensor plate while raypath 119 corresponds to a wave that passes into the borehole fluid in the annulus between the BHA and the borehole wall. The transducer 111 is provided with an absorptive backing 113 with an impedance that closely matches that of the transducer so as to reduce reflections from the back side of the transducer. In the example shown, a single transducer acts as both a transmitter and as a receiver, though this is not to be construed as limitation to the disclosure: separate acoustic transmitters and receivers may be used.

The present disclosure relies on the signals recorded by excitation of the transducer as an indication of gas in the borehole fluid. Free gas in the borehole fluid has three main effects on the acoustic properties of the fluid. The first effect is a reduction in density of the fluid. A more important effect is the dramatic reduction in the bulk modulus of the fluid (and hence the acoustic velocity). This is the phenomenon that is the basis for the so-called "bright spot" effect in hydrocarbon exploration wherein the presence of gas in a reservoir can produce strong reflections on seismic data. Basically, in a gas-liquid mixture, the average compressibility (the reciprocal of bulk modulus which is linearly related to the square of the acoustic velocity) is obtained by a weighted average of the compressibilities of the two fluids. The third effect that may be observed is the attenuation of the wave that actually propagates into the borehole and may be reflected by the borehole wall. However, by the time actual gas bubbles appear in the borehole at depth, it may be on the verge of a blowout. Accordingly, an objective of the disclosure is to determine the pressure kicks before gas comes out of solution in the borehole fluid.

Invasion of formation fluids into the borehole is usually the result of the formation pore pressure exceeding the fluid pressure in the borehole. This may be a harbinger of a blowout and remedial action is necessary. Due to the difference in the density and P-wave velocity of the borehole mud and the density and P-wave velocity of formation fluid, this influx is detectable. Specifically, the effect of invasion is to lower the bulk modulus and density of the fluid in the borehole. This translates into a change in the impedance (and the velocity) of the mud.

Figure 5:
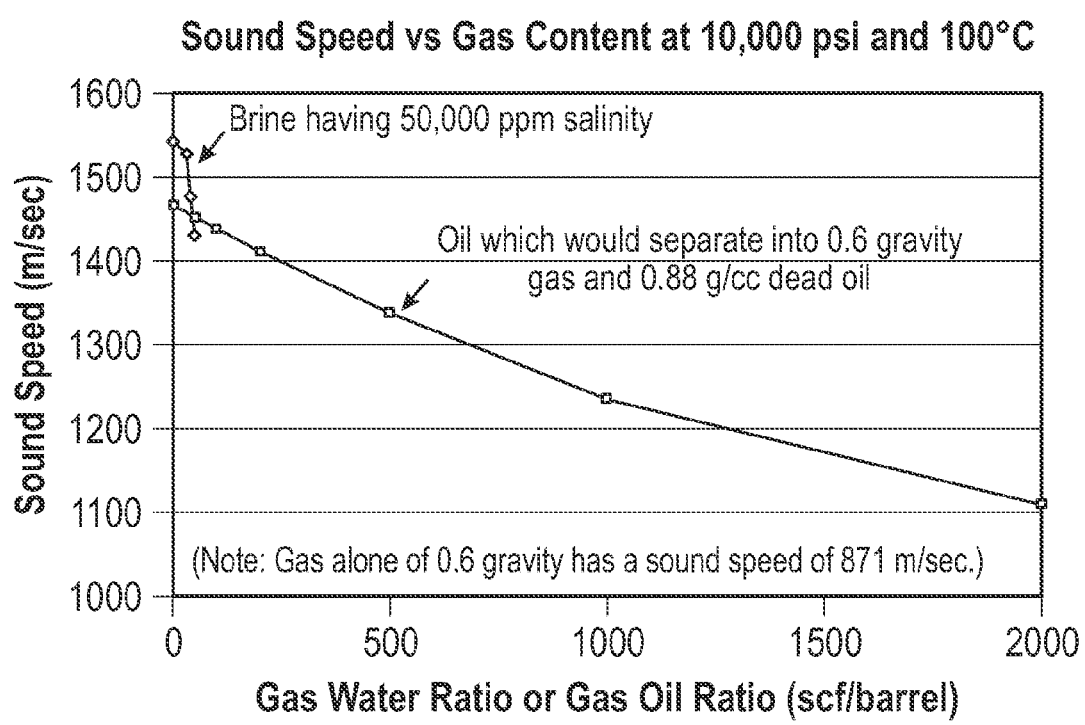
FIG. 5 (Prior Art) shows sound speed dependence on dissolved gas.

FIG. 5 shows representative examples of sound speed (ordinate) versus amount of dissolved gas (abscissa) using a model proposed by Batzle et al. Although, the Batzle equations were intended for formation brines and crude oils, for water based muds and for oil based muds they should provide the same trends in sound speed with increasing dissolved gas. For the present disclosure, the model of Batzle et al. may be used with appropriate parameters for drilling fluid, live oil (oil with dissolved gas) and dead oil. This is not to be construed as a limitation of the present disclosure and other models for predicting the elastic properties of fluid mixtures may be used. Han & Batzle shows correlations of velocity and density to API gravity, Gas-Oil Ratio (GOR), Gas gravity and in situ pressure and temperatures. This is an example of another model that may be used with the method of the present disclosure. In practice, the empirical cross-plots may be stored in the form of a table and a table lookup performed to determine the presence of gas in the borehole fluid.

Such a model may also be used for predicting the properties of a mixture of drilling mud and formation fluid. The net result of a fluid influx is to change the impedance of the borehole fluid.

Figure 4A:
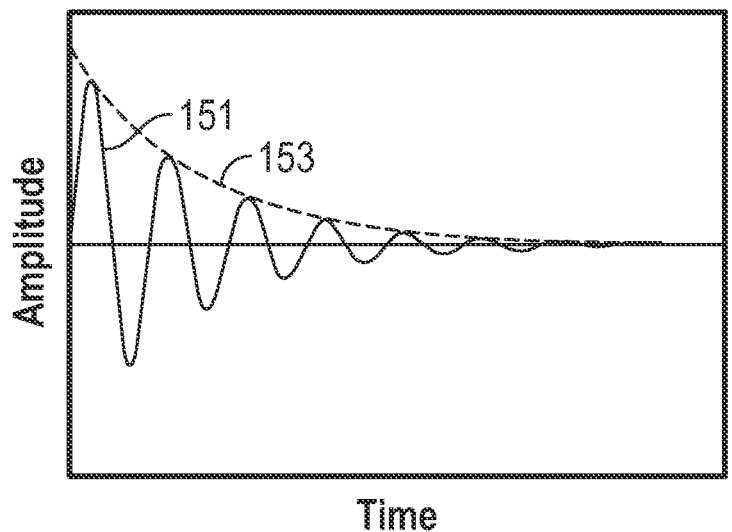
FIGS. 4A and 4B show exemplary signals using the acoustic transducer of FIG. 2 when the impedance of the borehole fluid is (a) close to that of the sensor plate, and (b) different from that of the sensor plate.
Figure 4B:
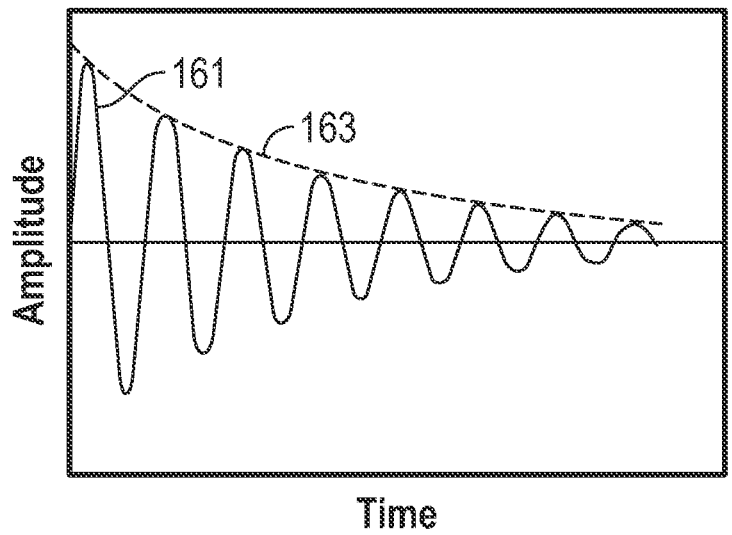

Those versed in the art and having benefit of the present disclosure would recognize that if the impedance of the fluid is close to that of the plate, then reverberations of the plate caused by excitation of the transducer will decay very rapidly. This is shown schematically in FIG. 4A by the decay curve 153 of the reverberatory signal 151. If, on the other hand, the impedance of the fluid is greatly different from that of the plate, the reverberations 161 die out more slowly 163. The relative decay can be quantified by the Q (or quality factor) of the plate. This is something that can be readily measured using prior art techniques.

Maximum sensitivity is obtained by using a plate whose acoustic impedance is as close as possible to the fluid impedance so as to minimize the impedance contrast with the fluid, which typically ranges from 1500 kRayls for a light drilling fluid to 2300 kRayls for a heavy drilling fluid. The plate must also be thermally stable, mechanically tough, and chemically resistant. Among polymers, a polyimide ranging from 2400 to 2920 kRayls or a poly(etherether-ketone) ranging from 3122 to 3514 kRayls are good candidates. Another polymer that is a good candidate is polymethlypentene (tradenamed TPX, which is made by Mitsui) that has an acoustic impedance of 1840 kRayls. Pyrolytic graphite (6 480 kRayls depending on orientation) from GE Advanced Ceramics is a good candidate. Among metals, titanium (about 24 000 kRayls) or aluminum (about 15 800 kRayls) are good candidates. The inside face of the plate is in contact with oil in a pressure-balanced enclosure, with known acoustic characteristics. Incoming water oil or gas is expected to lower the acoustic impedance markedly. The instrument takes a reading every second and stores it in memory for 2 hours. In one embodiment of the disclosure, if the instrument observes a change in acoustic impedance of 10% or more during a 2 minute interval from the extrapolated value of the preceding hour then it sends a high priority alarm and a series of informative values of the acoustic impedance from say intervals of 20 seconds preceding the alarm. The use of a 10% change in acoustic impedance is for exemplary purposes only and other criteria could be used for sending an alarm.

Figure 6:
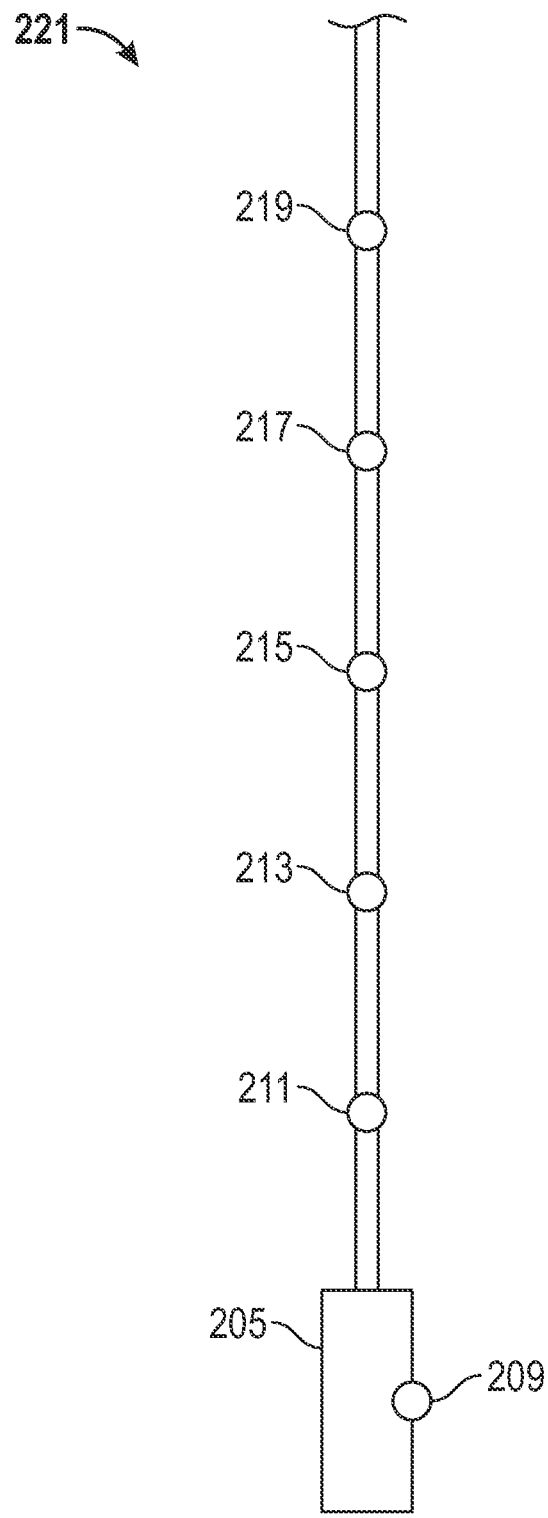
FIG. 6 shows an embodiment of the disclosure in which a plurality of acoustic transducers are disposed along the drill collar.

Another embodiment of the disclosure is illustrated in FIG. 6. Here, the BHA 205 is provided with a transducer arrangement 209 of the type discussed above and additional transducer assemblies 211, 213, 215, 217, 219 are disposed along the drill collar 221. These are in electrical communication with each other and with a processor at the surface using wired-pipe telemetry (though other telemetry methods may be used). The impedance of the mud is estimated by determining the Q of the resonant plate. The velocity of P-waves in the mud may be measured using, for example, the apparatus described in U.S. patent application Ser. No. 10/298,706 of Hassan et al., having the same assignee as the present disclosure and the contents of which are incorporated herein by reference.

The discussion above has focused on one effect of gas influx on borehole fluid properties, namely, fluid impedance. However, as noted above, the velocity of compressional waves in the borehole fluid is also affected by gas influx. U.S. patent application Ser. No. 11/194,365 of DiFoggio, having the same assignee as the present disclosure and the contents of which are incorporated herein by reference, discloses a method of estimating a fluid property with a sampling vessel using an estimated velocity of an acoustic signal. The principles disclosed therein are also applicable for MWD applications.

Before discussing this embodiment, it is worthwhile to point out differences between oil-based mud and water-based mud insofar as the effect of gas influx is concerned. Water based muds can only accommodate approximately 50 cubic feet of dissolved gas per barrel of mud whereas the oil based muds can accommodate many times more dissolved gas. If only dissolved gas is present (but no free gas, which means no bubbles), sound speed will drop faster in water based mud than in oil based mud with increasing gas concentration (FIG. 5). For either type of mud, once gas comes out of solution, the bulk modulus of the bubbly mixture of liquid and gas will become comparable to the bulk modulus of the gas alone. It is analogous to putting a weak spring in series with a stiff spring, which creates a composite spring whose stiffness is approximately that of the weak spring. However, the density of the bubbly mixture is only slightly reduced. For fluids, sound speed can be calculated as the square root of ratio of the bulk modulus (stiffness) to the fluid density. Therefore, as gas comes out of solution, there is a marked decrease in sound speed but it does not drop to the sound speed of gas alone. Because the detection of gas influx only requires a detection of a change in sound speed over a short time, we only need high precision (resolution) measurements of sound speed for gas influx detection. Of course, to quantify the amount of gas influx, we would also need good sound speed accuracy. The acoustic impedance also changes as gas comes out of solution.

Figure 7:
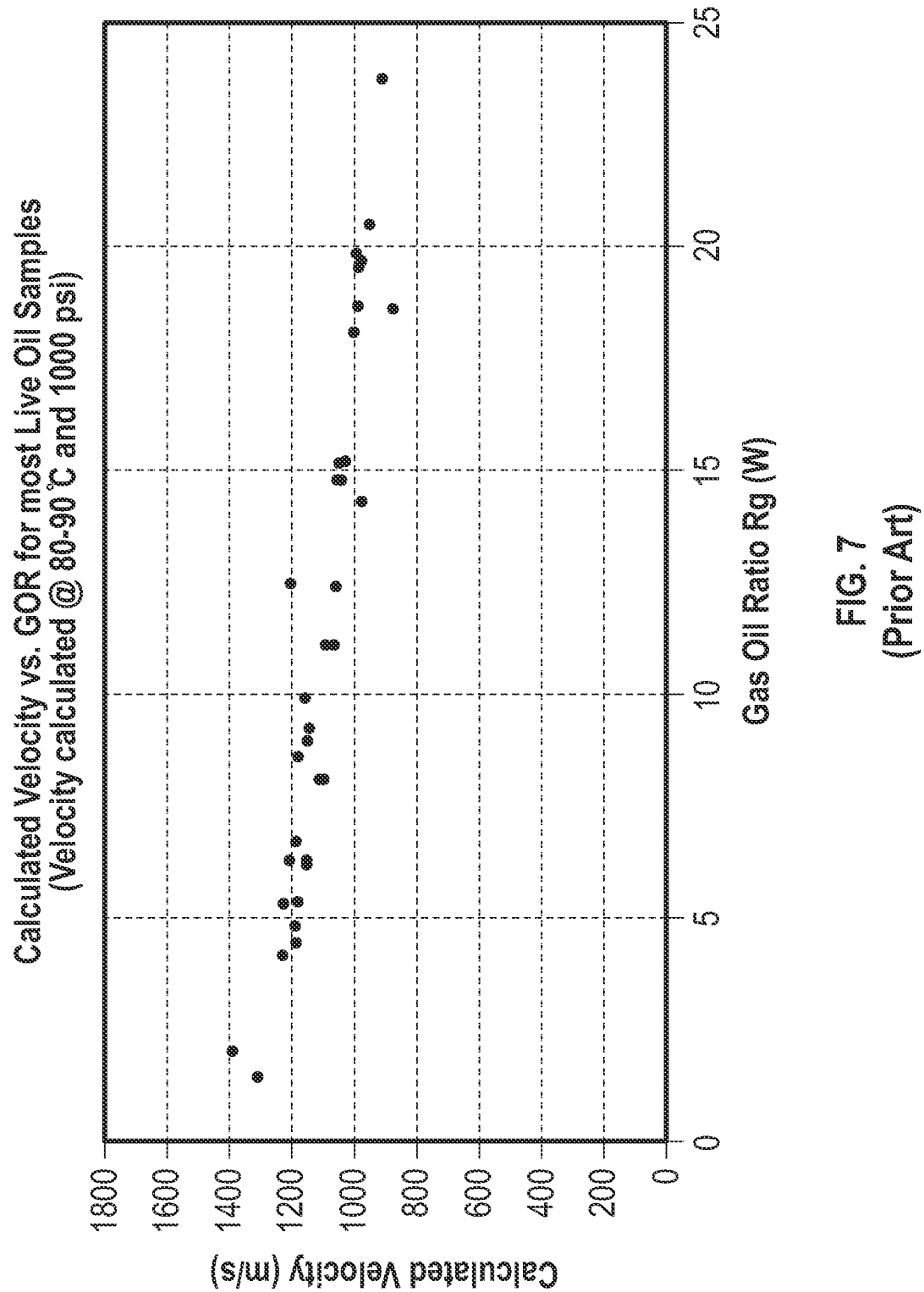
FIG. 7 (Prior Art) is an exemplary plot of velocity as a function of gas-oil ratio.

In contrast, FIG. 7 shows velocity for a gas-oil mixture. The gas remains in solution over a wide range of saturations. Those versed in the art would recognize that direct measurements of velocity using pulse transmission measurements are difficult in the presence of bubbles. This means that in oil-based muds, it would be easier to measure the acoustic velocity over a wide range of gas saturation than for water-based mud.

Figure 8:
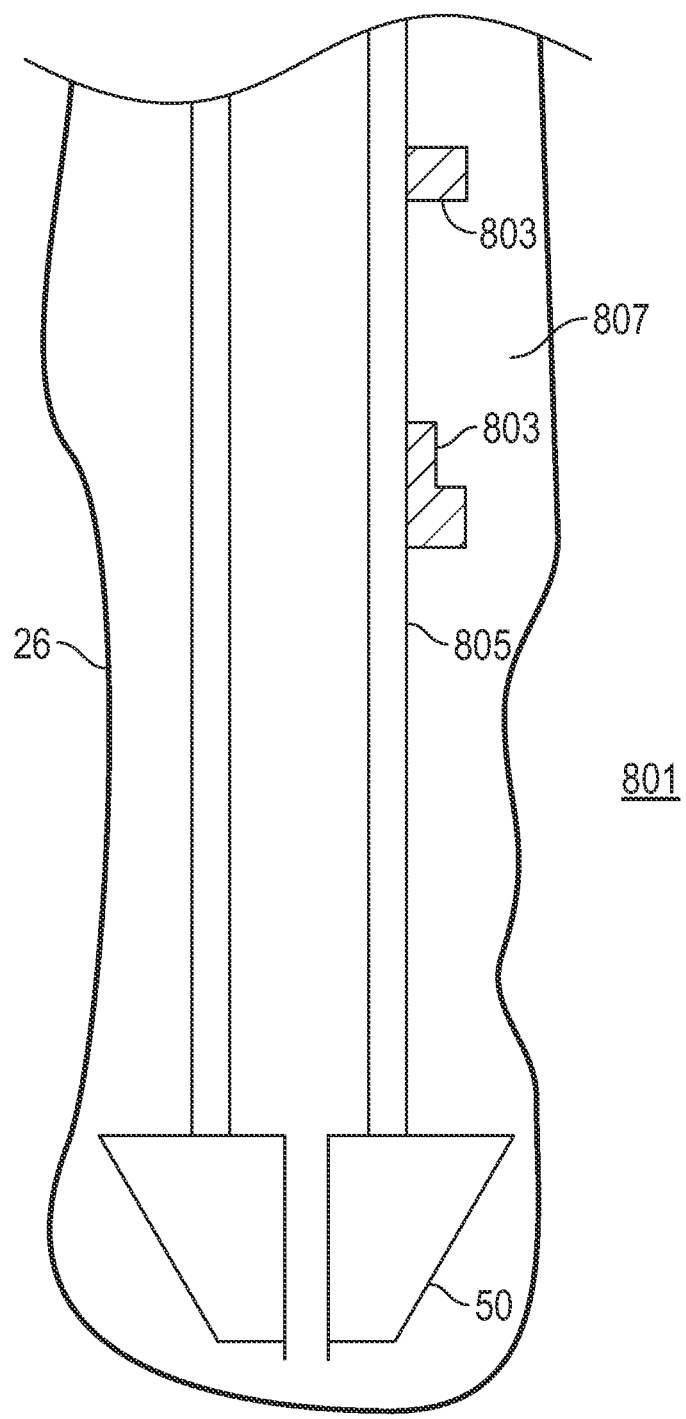
FIG. 8 shows an exemplary arrangement of a transducer for measuring travel-times in the borehole fluid.

DiFoggio discloses an arrangement for measuring fluid velocities in a sample chamber on a BHA or a wireline assembly. In the present disclosure, instead of using a sample chamber, a transducer assembly is positioned on the outside of the drill collar. This is illustrated in FIG. 8 which shows a borehole 26 in an earth formation 801. The acoustic sensor assembly 803 is on the outside of the drillstring 805 so as to measure the acoustic velocity of mud in the annulus 807.

Figure 9A:
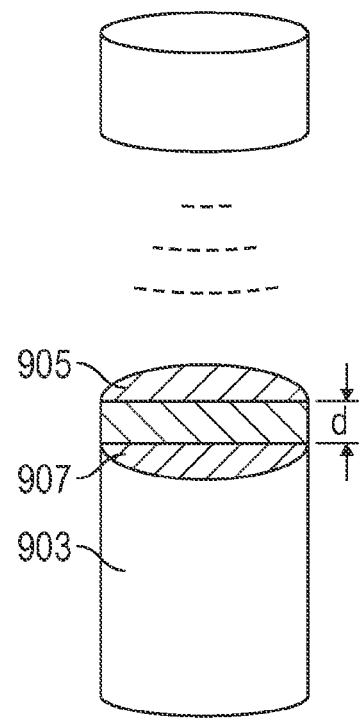
FIG. 9A illustrates the principle of a stepped transducer.
Figure 9B:
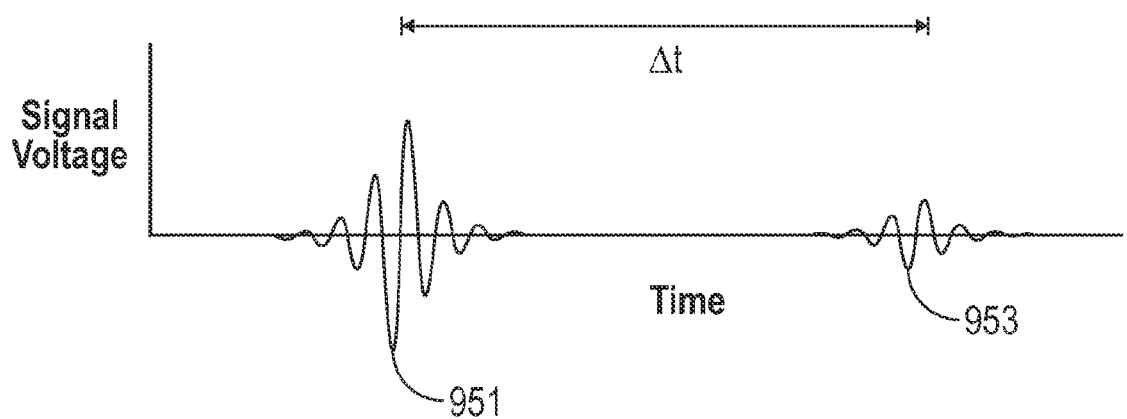
FIG. 9B illustrates an exemplary signal with the stepped transducer of FIG. 9A.

The acoustic sensor assembly 803 is shown in more detail in FIG. 9A. The acoustic sensor assembly 803 comprises a transducer 901 and a stepped reflector 903. The stepped reflector includes a protruding portion 905 and a recessed portion 907 that is a distance "d" further away from the transmitter than is the protruding portion. The transmitter generates an acoustic pulse depicted by 909. The stepped reflector 903 produces two signals. The reflected signal received by the transducer 901 is shown in FIG. 9B. The first arrival 951 is a result of the reflection of the pulse 909 at the protruding portion 905 of the reflector. The second signal 953 is a result of the reflection of the acoustic pulse 909 at the recessed portion 907 of the reflector. The depth of the recess d and the time difference between the two arrivals ΔT gives the velocity of the acoustic pulse in the mud.

$$v = 2d/\Delta t$$

There are prior art teachings of using travel time measurements over two different distances to estimate the fluid velocity. These suffer from the drawback that two different source pulses are involved, either from two different transducers or from the same transducer at two different times. The two different source pulses inevitably have somewhat different waveforms, so that estimating a difference of the travel times to extremely high precision is limited by the differences between those two source waveforms. This is particularly true in the present case where the acoustic pulses are transmitted through an attenuative and dispersive medium, namely, the borehole fluid. With the present transducer, the problem of source waveform variability is eliminated because the arrivals at the two different times, which are being compared, are both echoes of the very same generated acoustic pulse. There are several waves to estimate the travel time difference Δt.

In one embodiment of the disclosure, an autocorrelation of the received signal is performed and a peak value of the autocorrelation gives the travel time. Alternatively, a cross-correlation of two different windows of the received signal is used, the two different windows being selected based on an expected arrival time for the acoustic pulse in order to avoid spurious aliasing. The more closely spaced the time channels for collecting the received signal, the better that the travel time resolution will be. To obtain sub-channel resolution, we interpolated the peak position between time channels. The conceptual basis for sub-channel resolution is to fit a polynomial to the autocorrelation function in the neighborhood of the peak and then to find the zero crossing (the root) of the first derivative of that polynomial, which is the interpolated peak position. Because the time channels were uniformly spaced, we were able to use the computationally-simple Savitzky Golay method to compute the first derivative, f', of the fitting polynomial at two time steps (the one just left and the one just right of the peak), and then to perform linear interpolation of the first derivative to obtain its zero crossing, which is the interpolated peak position, $x_P$. That is, $f'(x_L)/[-f'(x_R)]=d_L/d_R$, where $d_L=x_P-x_L$ and $d_R=x_R-x_P$ and $d_L+d_R=x_R-x_L$. Of course, quadratic interpolation or iterative root finding could also have been used to find $x_P$. Using such correlation and sub-channel interpolation methods, the transducer structure of FIG. 9A has given measurements of velocity in water with a precision of 25 parts per million (ppm).

Such a precision may be hard to achieve in a borehole environment due to the attenuative and dispersive nature of the signals in mud. There are two main causes for this dispersion and attenuation. The first is due to the presence of solid particles in the mud that absorb acoustic signals. A second cause of dispersion and attenuation is the presence of gas bubbles. Elastic theory predicts that as long as concentration of gas bubbles is low and the gas bubbles are much smaller than a quarter of the wavelength of the acoustic pulses, the reflections of the acoustic pulse would still be detectable. As the concentration of gas bubbles increases and their size increases, no reflected signals would be detectable.

For the situation where there is a detectable reflection, the estimate of the travel time can be improved using deconvolution methods. Specifically, in one embodiment of the disclosure, a Wiener deconvolution of the second arrival of the received signal is performed using, as a reference wavelet, the first arrival. See Honvarvar et al. (2008).

In another embodiment of the disclosure, a travel time is measured for the reflection from the protruding portion of the reflector. This may be done if the reflection from the recessed portion is too weak. In such a case, the distance between the transmitter and the protruding portion of the reflector is used. A single reflection may also be used with a transducer assembly that has a flat reflector. In such situations, the estimate of the travel time may be improved using the method disclosed in DiFoggio. Specifically, the raw amplitude data can be first processed by applying a digital bandpass filter to reject any frequencies that are not close to the acoustic source frequency. For example, for a 10 MHz acoustic source and a 40 MHz sampling frequency, one could apply a 9-11 MHz digital bandpass filter. Next, one can compute the square of the amplitude at each sampling time, which corresponds to the energy received at that time. Then, one can generate a cumulative sum of squares (CSS) of these amplitudes, which is the cumulative sum of energy received up until that time. The digital bandpass filtering and cumulative sum of squares have already smoothed the raw data and removed some noise. We can further smooth the filtered cumulative sum of squares data and also take the first and second derivatives of the CSS using the Savitzky-Golay method (Savitzky and Golay, Analytical Chemistry, Vol. 36, No. 8, July 1964). The first derivative of CCS generates a series of Gaussian-looking peaks. The second derivative of the CSS are the first derivatives of the Gaussian peaks, whose zero crossings (roots) represent the interpolated peak positions. Smoothing the data and the utilization of the Savitzky-Golay method helps to reduce noise from the desired signal.

Figure 11:
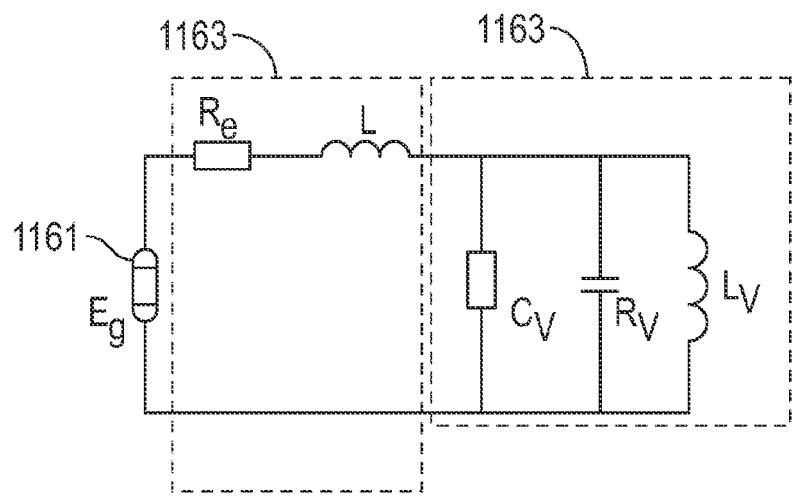
FIG. 11 (Prior Art) is an equivalent circuit of a transducer in contact with a borehole fluid.

Returning now to the issue of direct measurement of impedance, another embodiment of the disclosure makes direct measurements without relying on measuring the resonance of a sensor plate. FIG. 11 is an equivalent circuit of a transducer in contact with a borehole fluid, discussed in U.S. patent application Ser. No. 11/447,746 of Dubinsky et al., having the same assignee as the present application. The transducer is represented by the RL circuit 1163 that has an impedance $Z_e$ given by $Z_e=R_e+X_{Le}=R_e+j\omega L$. The power source $E_g(\omega t)=Re[|E_g(\omega t)|exp(j\omega t)]$ is denoted by 1161, while the interaction of the transducer with the fluid is represented by a parallel RLC load circuit 1165. Given this electrical equivalent circuit, by exciting the transducer at a plurality of angular frequencies $\omega_i=\omega_1,\omega_2,\omega_3, \ldots$, and measuring the plurality of phase shifts $\phi_i=\phi_1,\phi_2,\phi_3, \ldots$, between the applied voltages $E_g(\omega t)=Re[|E_g(\omega_i t)|exp(j\omega_i t)]$ and the respective currents $i_e(\omega_i t+\phi_i)=Re[|i_e(\omega_i t\phi_i)|exp(j(\omega_i t+\phi_i))]$ in the RL circuit 1163 portion, it is possible to completely characterize the equivalent impedance $$Z_v = \frac{1}{1/R_v + j\omega C_v + 1/(j\omega L_v)}$$

of the parallel RLC load circuit 1165, giving the impedance of the mud $R_v$.

Figure 10:
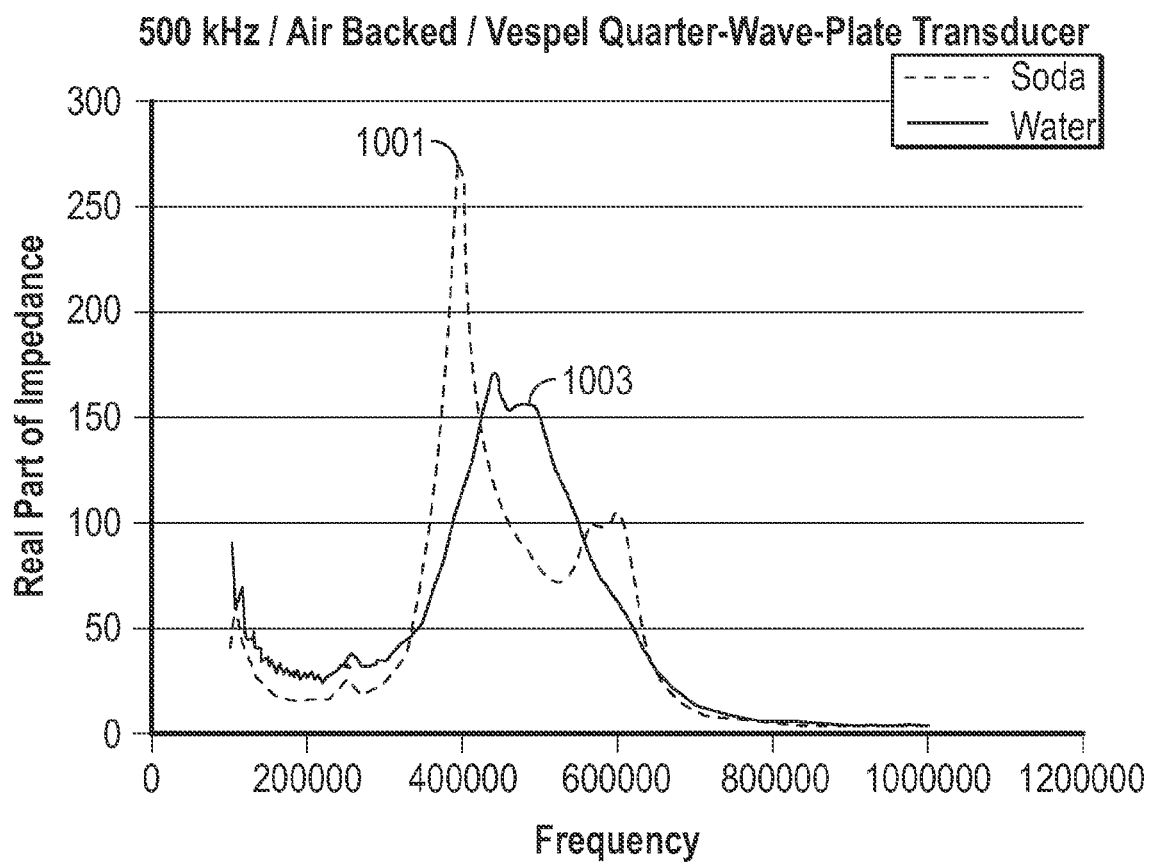
FIG. 10 shows measurements of impedance at the input of a piezoelectric transducer as a function of frequency in different fluids.

FIG. 10 shows actual measurements of the impedance of an exemplary piezoelectric transducer at different frequencies. The curves 1001 and 1003 are the real (in-phase) impedance for a transducer immersed in soda (containing dissolved CO2 but no visible bubbles) and in water respectively. The imaginary (out-of-phase) impedance could also be plotted. There is a clear difference in the peak of the real impedance for soda, which contained dissolved gas, compared to water. The narrow bandwidth of the resonance for the soda curve 1001 is a result of a high quality factor Q of the sensor due to the low impedance of the soda water at that frequency. This experiment could be repeated under pressure to insure that all bubbles, including those that might be too small to see, have been crushed.

Figure 12:
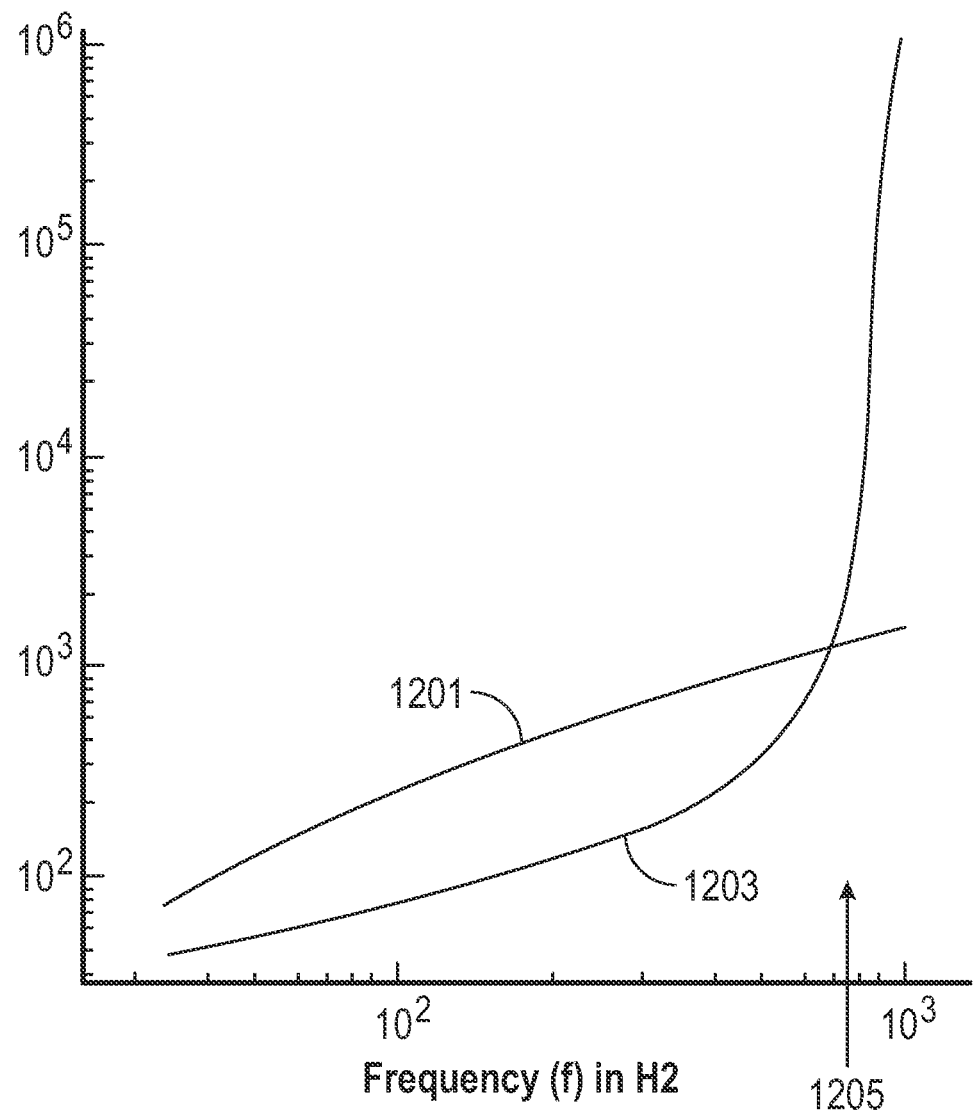
FIG. 12 (Prior Art) shows the effect of bubble size on attenuation.

Turning to FIG. 12, data are shown of the effect of air bubbles on acoustic signals propagating through water. These measurements were made at frequencies of up to 1 kHz. The curve 1201 corresponds to a bubble radius of 0.002 ft (0.61 mm) and the curve 1203 to a bubble radius of 0.014 ft (4.27 mm). The abscissa is the frequency and the ordinate is the product of attenuation and sound velocity, i.e., the attenuation in dB per second. The lower frequency measurements generally show lower attenuation, but the attenuation increases rapidly as a resonance frequency 1205 is approached.

Based on the discussions above, it can be seen that detection of gas influx is relatively easy to do when oil-based-mud (OBM) is used. Pulse transmission techniques may be used, and generally give a more precise estimate of gas saturation than do impedance measurements. Above the bubble point, pulse transmission techniques have some difficulty in getting measurable signals. When water-based-mud (WMB) is used, due to the low solubility of gas in water, it becomes more difficult for pulse transmission techniques to accurately measure saturation, particularly as the gas saturation and/or bubble size increases. Impedance measurements, while less precise, can give estimates of gas saturation above bubble point. With either method, it is important to monitor the gas saturation during drilling operations. When no detectable reflection, or a severely attenuated reflection is received by the transducer, this is referred to as a null output and the processor indicates the presence of bubbles in the fluid. The margin of safety is somewhat larger for OBM.

Figure 13:
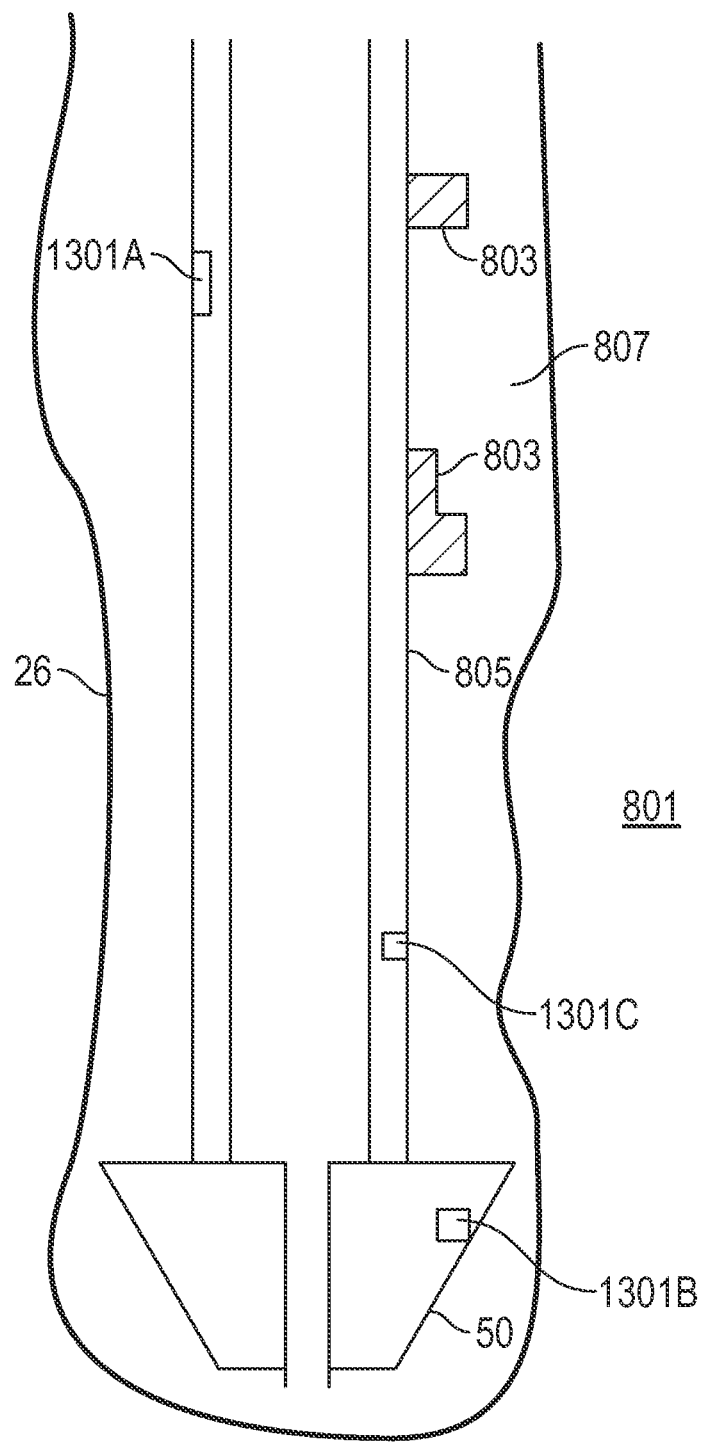
FIG. 13 shows an exemplary embodiment of a drill string having various sensors usable for detecting a gas influx event using acoustic velocity and temperature measurements.

FIG. 13 shows an exemplary embodiment of a drill string 805 having various sensors usable for detecting a gas influx event using acoustic velocity and temperature measurements. The drill string includes the drill bit 50, an acoustic sensor 803 comprising an acoustic transducer and a stepped acoustic reflector, and at least one temperature sensor 1301A-C. The drill string may further include a processor such as discussed with respect to FIG. 1 that is configured to receive measurements obtained at the acoustic sensor and the temperature sensor and to detect the gas influx event using the received measurements and the methods discussed herein. The acoustic sensor measures the acoustic velocity of the fluid in the annulus 807. The temperature sensor measures the temperature of the fluid in the annulus 807. The acoustic sensor and the temperature sensor may be disposed at a location suitable for measuring acoustic velocity and temperature of the borehole fluid in the annulus between the drill string 805 and the borehole wall 26. In one embodiment, the temperature sensor, such as temperature sensor 1301A is disposed at substantially the same axial location of the drill string as the acoustic sensor 803. Alternately, the temperature sensor may be disposed within the drill bit 50 such as temperature sensor 1301B or proximate the drill bit 50 such as temperature sensor 1301C.

The presence of gas from a gas influx event causes a change in an acoustic velocity of the borehole fluid as well as a change in a temperature of the borehole fluid. Thus, a measured change in a temperature of the borehole fluid may be used to confirm a gas influx event that is detected using a measured change in the acoustic velocity of the borehole fluid.

Figure 14A:
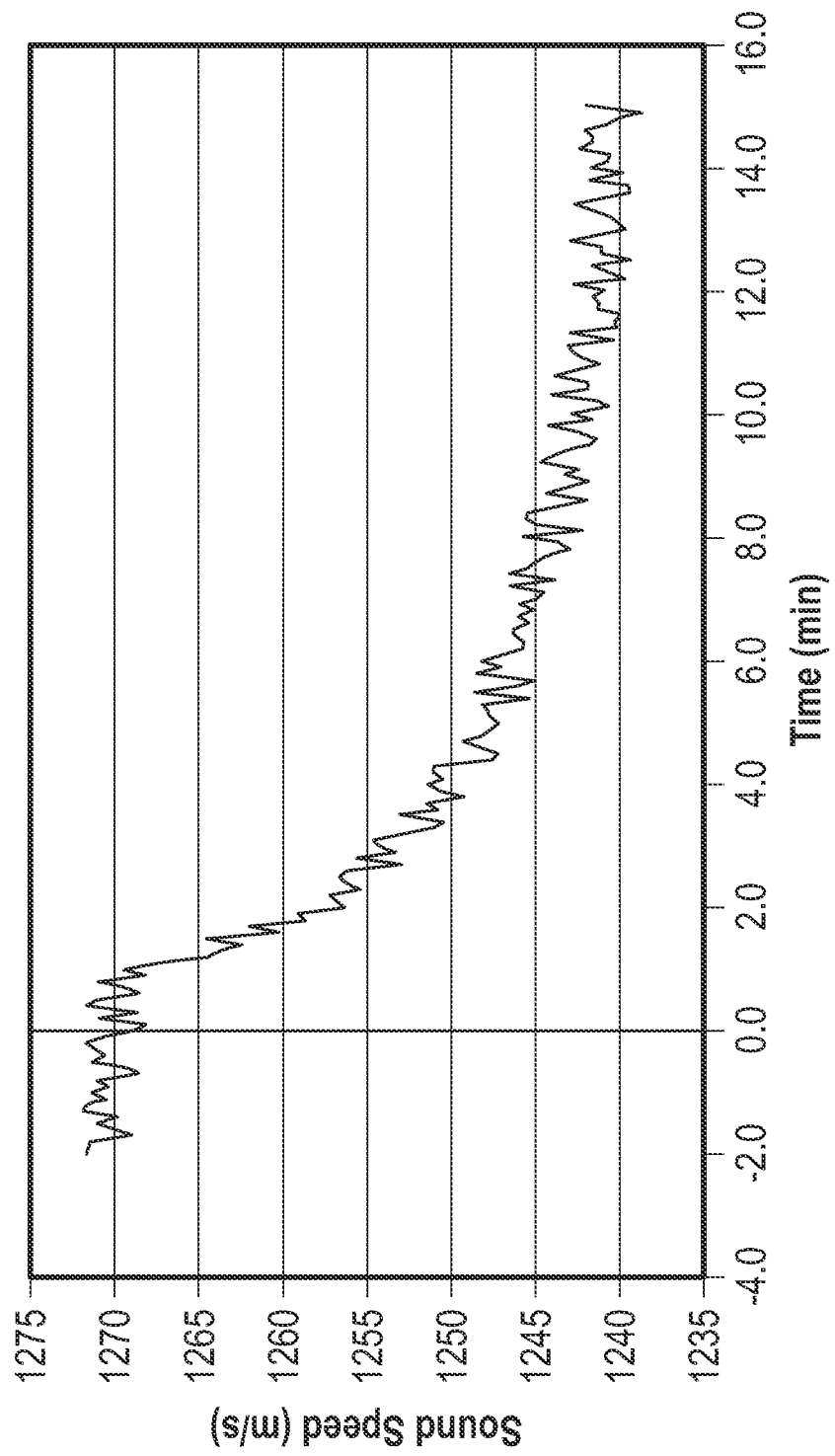
FIGS. 14A and 14B show exemplary graphs of acoustic velocity and temperature, respectively, that may be used to determine an influx of gas into a borehole fluid.
Figure 14B:
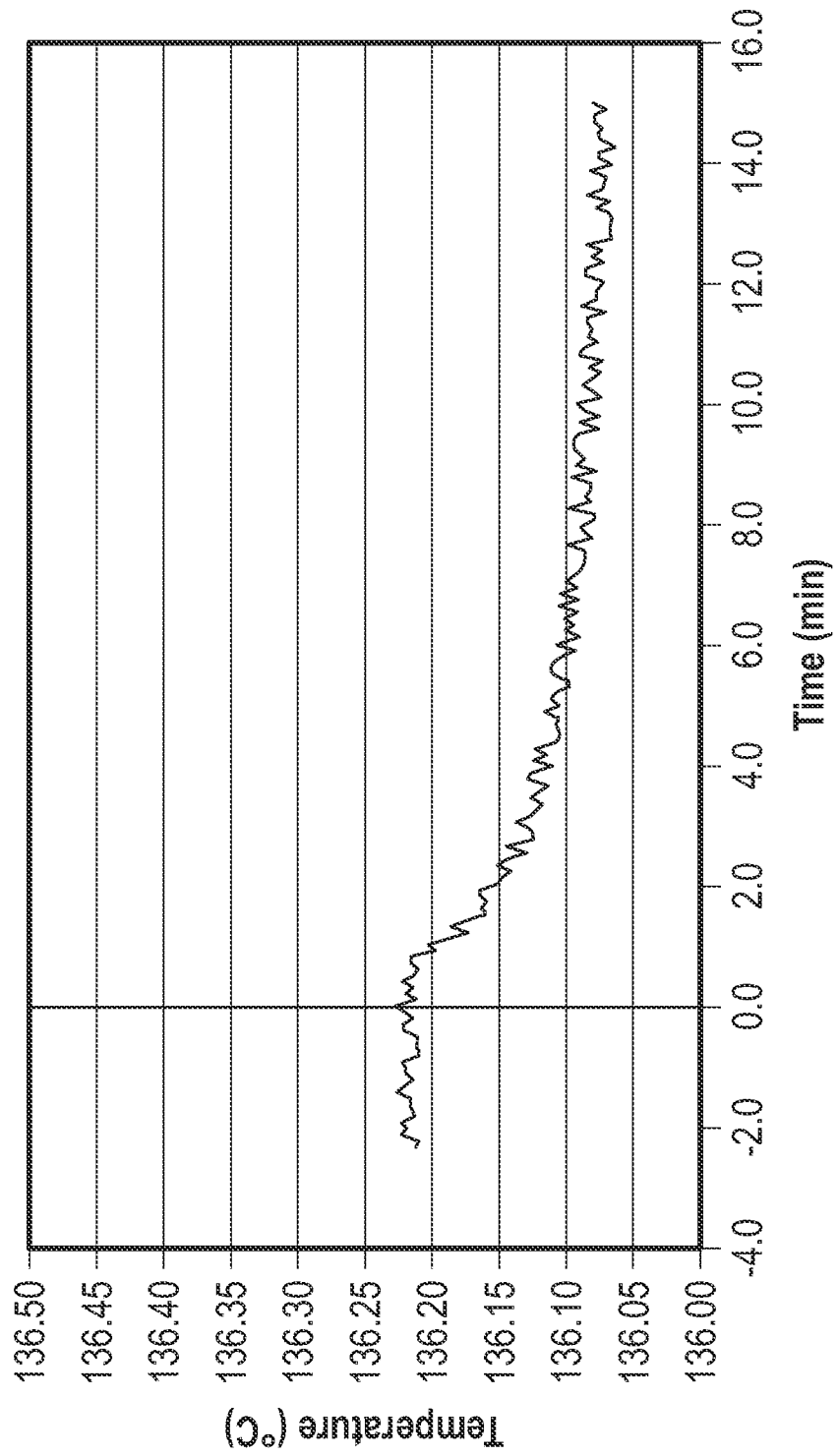

FIGS. 14A and 14B show exemplary graphs of acoustic velocity and temperature, respectively, that may be used to determine an influx of gas into a borehole fluid. The acoustic velocity of the borehole fluid changes from a first velocity to a second velocity when gas enters the borehole fluid (at t=0). In the exemplary graph of FIG. 14A, the acoustic velocity changes from about 1270 msec to about 1240 msec. Additionally, the temperature of the borehole fluid changes from a first temperature to a second temperature when the gas enters the borehole fluid. In the exemplary graph of FIG. 14B, the temperature changes from about 136.20° C. to about 136.05° C. Although, the changes are shown as a drop in the values of the measured properties, the changes can also include rises in these values. If the acoustic sensor and the temperature sensor are placed at the same locations, these changes may be detected at substantially the same time. If the acoustic sensor and the temperature sensor are placed at separate locations, then the changes may be detected at different times. However, the time difference can be removed by shifting the graph of the temperature with respect to the graph of the acoustic velocity by a determinable amount.

Figure 14C:
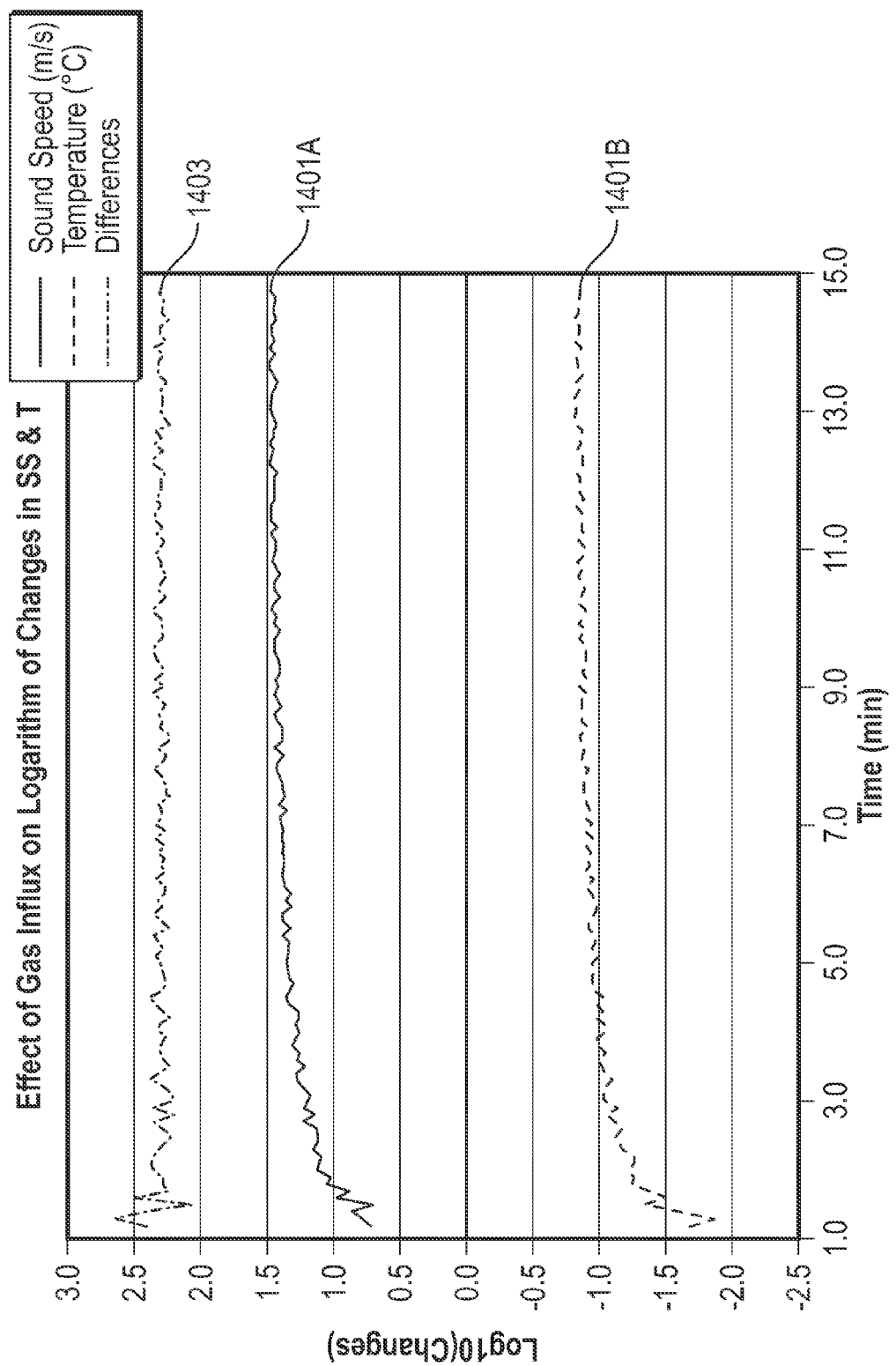
FIG. 14C shows logarithmic values derived from the exemplary graphs of FIGS. 14A and 14B.

FIG. 14C shows logarithmic values derived from the exemplary graphs of FIGS. 14A and 14B. Curve 1401A is a logarithm of the acoustic velocity values of FIG. 14A and curve 1401B is a logarithm of the temperature values of FIG. 14B. Curve 1403 is a difference between curve 1401A and curve 1401B. The substantially constant value of curve 1403 indicates that the acoustic velocity and the temperature are changing at substantially the same rate and therefore that the changes in the acoustic velocity and in the temperature result from the same effect, i.e., a gas influx event. In the event that the temperature is rising (instead of falling) as gas influx occurs, for the purposes of comparing temperature and acoustic velocity changes with time, the temperature curve can be subtracted from a constant temperature value to produce a complementary temperature curve. This complementary temperature curve declines with time similar to the decline of the acoustic velocity curve with time shown in FIG. 14B.

Figure 15A:
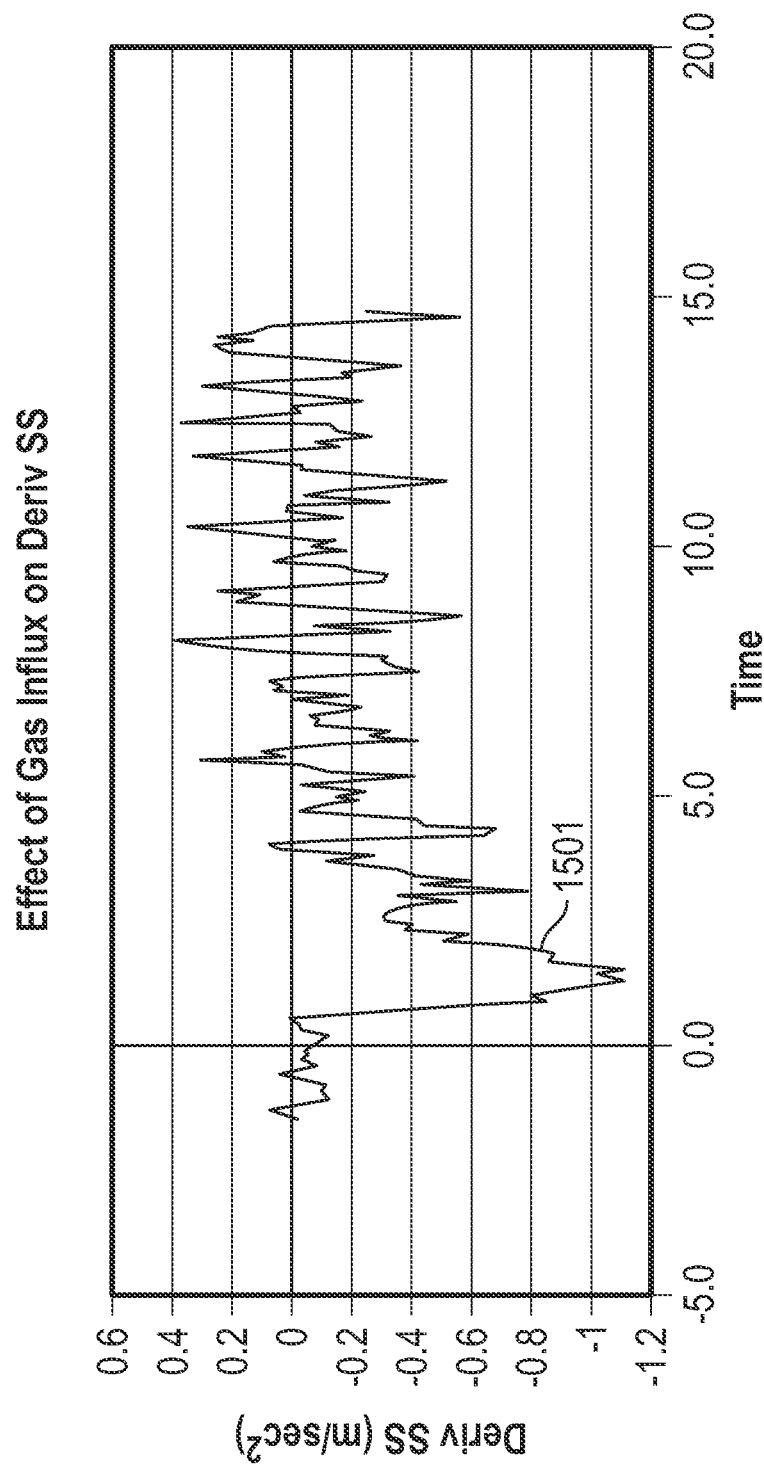
FIG. 15A shows a graph of a change in acoustic velocity values over time.

FIG. 15A shows a graph of a derivative of acoustic velocity values against time. FIG. 15B shows a graph of a derivative of borehole fluid temperature values against time. The derivative values crosses over a threshold value upon a gas influx event occurring at t=0. For example, graph 1501 drops below an exemplary threshold value of −0.8 m/sec$^2$ at about t=1 following the gas influx event and graph 1503 drops below an exemplary threshold value of −0.01° C./sec at about t=1 following the gas influx event. The gas influx event is confirmed by having both the acoustic velocity and temperature crosses over these selected threshold values. Although the exemplary graphs indicate the occurrence of the gas influx event when graphs 1501 and 1503 drop below the threshold value, an alternate graph can be used in which one or more graphs rise above a selected value to indicate the gas influx event.

Figure 16:
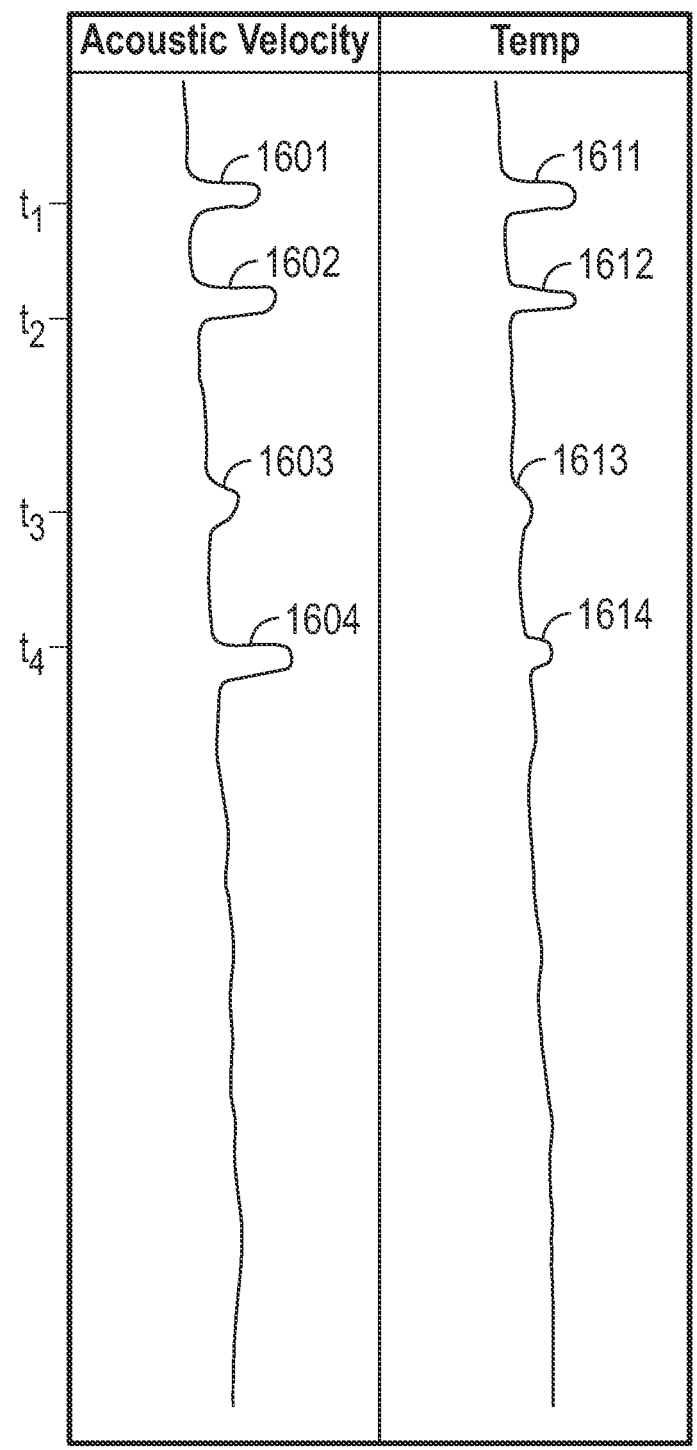
FIG. 16 shows exemplary graphs of acoustic velocity and temperature over time.

FIG. 16 shows an exemplary graph of acoustic velocity vs. time and an associated exemplary graph of temperature vs. time displaying a number of gas influx events. Acoustic velocity spikes 1601-1604 occur at times $t_1$-$t_6$, respectively. Similarly, temperature spikes 1611-1614 occur at times $t_1$-$t_6$, respectively. Typically, a spike in the acoustic velocity occurs simultaneously with a spike in the temperature when they result from a same event. The height of each spike may be compared to a selected threshold value to indicate the presence of gas. As an example, at $t_1$ and $t_2$, respectively, acoustic velocity spikes 1601 and 1602 are greater than a selected acoustic velocity threshold value and temperature spikes 1611 and 1612 are greater than a selected temperature threshold value. Thus, a gas influx event is confirmed at times $t_1$ and $t_2$. In contrast, spikes 1603 and 1613 are not greater than their respective threshold values, and thus no gas influx event is detected at $t_3$. Acoustic velocity spike 1604 is greater than the acoustic velocity threshold, but corresponding temperature spike 1614 is not greater than the temperature threshold value. Therefore, a gas influx event is not detected at $t_4$. In various embodiments, acoustic velocity and temperature measurements are obtained at time intervals close enough to provide a sufficient resolution to record the spikes of FIG. 16. The height of the spikes may be determined by comparing values over several time intervals.

The processing of the data may be accomplished by a downhole processor and/or a processor at the surface. Alternatively, measurements may be stored on a suitable memory device and processed upon retrieval of the memory device for detailed analysis. Implicit in the control and processing of the data is the use of a computer program on a suitable machine readable medium that enables the processor to perform the control and processing. The machine readable medium may include ROMs, EPROMs, EAROMs, Flash Memories and Optical disks. All of these media have the capability of storing the data acquired by the logging tool and of storing the instructions for processing the data. It would be apparent to those versed in the art that due to the amount of data being acquired and processed, it is impossible to do the processing and analysis without use of an electronic processor or computer.

Therefore, in one aspect, the present disclosure provides a method of detecting a gas influx event in a borehole fluid during drilling operations that includes: obtaining a measurement of an acoustic velocity of the borehole fluid at an acoustic sensor disposed in a borehole; obtaining a measurement of temperature of the borehole fluid at a temperature sensor disposed in the borehole; and comparing the measurement of the acoustic velocity of the borehole fluid to the measurement of the temperature of the borehole fluid to detect the gas influx event. In one embodiment, the gas influx event is detected when a change in the acoustic velocity exceeds a selected acoustic velocity threshold and a change in the temperature exceeds a selected temperature threshold. The change in the acoustic velocity exceeds the selected acoustic velocity threshold and the change in the temperature exceeds the selected temperature threshold at substantially a same time. In one embodiment, the measurement of acoustic velocity of the borehole fluid is obtained by generating an acoustic pulse in the borehole fluid at a downhole location; reflecting the generated acoustic pulse from at least two reflecting surfaces of a stepped reflector in the fluid to provide at least two reflected pulses; and determining the acoustic velocity of the borehole fluid from a difference in arrival time of the at least two reflected pulses. The method may further include providing a logarithmic plot of the acoustic velocity versus time and to a logarithmic plot of the temperature (or of the complementary temperature) versus time. The method may alternatively include comparing a first derivative of the acoustic velocity to a selected threshold value and comparing a first derivative of the temperature to a selected threshold value. The acoustic sensor and the temperature sensor are disposed in an annulus between a drill string and a borehole wall. The temperature sensor may be disposed at one of: (i) in a drill bit; (ii) proximate the drill bit; and (iii) proximate a bottomhole assembly.

In another aspect, the present disclosure provides an apparatus for detecting a gas influx event in a borehole fluid during drilling operation that includes: an acoustic sensor configured to obtain a measurement of an acoustic velocity of the borehole fluid; a temperature measuring device configured to obtain a measurement of a temperature of the borehole fluid; and a processor configured to compare the measurement of the acoustic velocity of the borehole fluid to the measurement of the temperature of the borehole fluid to determine a gas influx event. The processor may be further configured to detect the gas influx event when a change in the acoustic velocity exceeds a selected acoustic velocity threshold and a change in the temperature exceeds a selected temperature threshold. The processor may be further configured to detect the gas influx event when the change in the acoustic velocity exceeds the selected acoustic velocity threshold and a change in the temperature exceeds the selected temperature threshold at substantially a same time. In one embodiment, the acoustic sensor includes an acoustic transducer configured to generate an acoustic pulse in the borehole fluid and to detect an acoustic signal from the borehole fluid and a stepped reflector configured to provide at least two reflections of the generated acoustic pulse to the acoustic transducer. The processor may further compare a logarithmic plot of the acoustic velocity to a logarithmic plot of the temperature versus time. Alternatively, the processor may compare a first derivative of the acoustic velocity to a selected threshold value and compare a first derivative of the temperature to a selected threshold value. In one embodiment, the acoustic velocity sensor and the temperature sensor are disposed in an annulus between the drill string and borehole wall. The temperature sensor may be disposed at one of: (i) in a drill bit; (ii) proximate the drill bit; and (iii) proximate a bottomhole assembly.

In yet another aspect, the present disclosure provides a computer-readable medium having a set of instruction stored thereon that when read by a processor enable the processor to perform a method, the method including: receiving a measurement of an acoustic velocity of a borehole fluid from an acoustic sensor disposed in a borehole; receiving a measurement of temperature of the borehole fluid from a temperature sensor disposed in the borehole; and comparing the measurement of the acoustic velocity of the borehole fluid to the measurement of the temperature of the borehole fluid to detect a gas influx event.

While the foregoing disclosure is directed to the specific embodiments of the disclosure, various modifications will be apparent to those skilled in the art. It is intended that all such variations within the scope of the appended claims be embraced by the foregoing disclosure.

The invention claimed is:

1. A method of detecting a gas influx event in a borehole fluid during a drilling operation, comprising:
    generating acoustic pulses over a time period using an acoustic transducer disposed in a borehole;
    obtaining measurements of acoustic velocity of the acoustic pulses through borehole fluid over the time period at an acoustic sensor disposed in a borehole;
    obtaining measurements of temperature of the borehole fluid over the time period at a temperature sensor disposed in the borehole;
    determining a difference between a curve derived from the measurements of acoustic velocity and a curve derived from the measurements of temperature over the time period; and
    detecting the gas influx event when the acoustic velocity changes over the time period and the difference between the curve derived from the measurements of acoustic velocity and the curve derived from measurements of temperature is substantially constant during the time period.

2. The method of claim 1, wherein obtaining the measurements of acoustic velocity of the borehole fluid further comprises:
    generating the acoustic pulses in the borehole fluid at a downhole location;
    reflecting the generated acoustic pulses from at least two reflecting surfaces of a stepped reflector in the fluid to provide at least two reflected pulses; and
    determining the acoustic velocity of the borehole fluid from a difference in arrival time of the at least two reflected pulses.

3. The method of claim 1, further comprising determining a difference between a logarithmic plot of the acoustic velocity over the time period to a logarithmic plot of the temperature versus time over the time period.

4. The method of claim 1, wherein the acoustic sensor and the temperature sensor are disposed in an annulus between a drill string and a borehole wall.

5. The method of claim 1, further comprising disposing the temperature sensor at one of: (i) in a drill bit; (ii) proximate the drill bit; and (iii) proximate a bottomhole assembly.

6. The method of claim 1, further comprising detecting the gas influx event when a change in the acoustic velocity exceeds a selected acoustic velocity threshold and a change in the temperature exceeds a selected temperature threshold.

7. The method of claim 6, wherein the change in the acoustic velocity exceeds the selected acoustic velocity threshold and the change in the temperature exceeds the selected temperature threshold at substantially a same time.

8. The method of claim 6, further comprising comparing a first derivative of the acoustic velocity to a selected threshold value and comparing a first derivative of the temperature to a selected threshold value.

9. An apparatus for detecting a gas influx event in a borehole fluid during a drilling operation, comprising:
    an acoustic transducer disposed in the borehole configured to generate acoustic pulses in the borehole fluid over a time period and to obtain a measurement of an acoustic velocity of the acoustic pulses in the borehole fluid over the time period;
    a temperature sensor configured to obtain nail measurements of a temperature of the borehole fluid over the time period; and
    a processor configured to:
        determine a difference between a curve derived from the measurements of acoustic velocity and a curve derived from the measurements of temperature over the time period, and
        detect the gas influx event when the acoustic velocity changes over the time period and the difference between the curve derived from the measurements of acoustic velocity and the curve derived from measurements of temperature is substantially constant during the time period.

10. The apparatus of claim 9, wherein the acoustic transducer generates the acoustic pulses in the borehole fluid toward a stepped reflector configured to provide at least two reflections of the generated acoustic pulse to the acoustic transducer.

11. The apparatus of claim 9, wherein the processor is further configured to determine a difference between a logarithmic plot of the acoustic velocity over the time period to a logarithmic plot of the temperature over the time period.

12. The apparatus of claim 9, the acoustic transducer and the temperature sensor are disposed in an annulus between the drill string and borehole wall.

13. The apparatus of claim 9, wherein the temperature sensor is disposed at one of: (i) in a drill bit; (ii) proximate the drill bit; and (iii) proximate a bottomhole assembly.

14. The apparatus of claim 9, wherein the processor is further configured to detect the gas influx event when a change in the acoustic velocity exceeds a selected acoustic velocity threshold and a change in the temperature exceeds a selected temperature threshold.

15. The apparatus of claim 14, wherein the processor is further configured to detect the gas influx event when the change in the acoustic velocity exceeds the selected acoustic velocity threshold and a change in the temperature exceeds the selected temperature threshold at substantially a same time.

16. The apparatus of claim 14, wherein the processor is further configured to compare a first derivative of the acoustic velocity to a selected threshold value and compare a first derivative of the temperature to a selected threshold value.

17. A non-transitory computer-readable medium having a set of instruction stored thereon that when read by a processor enable the processor to perform a method of detecting a gas influx event in a borehole fluid during a drilling operation, the method comprising:
- receiving measurements of an acoustic velocity of a borehole fluid from an acoustic transducer disposed in a borehole resulting from a reflection of acoustic pulses generated by the transducer in the borehole fluid over a time period;
- receiving measurements of temperature of the borehole fluid over the time period from a temperature sensor disposed in the borehole;
- determining a difference between a curve derived from the measurements of acoustic velocity and a curve derived from the measurements of temperature over the time period; and
- detecting the gas influx event when the acoustic velocity changes over the time period and the difference between the curve derived from the measurements of acoustic velocity and the curve derived from measurements of temperature is substantially constant during the time period.

* * * * *